United States Patent [19]

Devas

[11] 4,240,162
[45] Dec. 23, 1980

[54] ENDOPROSTHETIC PATELLAR DEVICE

[75] Inventor: Michael B. Devas, Bexhill-on-Sea, England

[73] Assignee: National Research Development Corporation, London, England

[21] Appl. No.: 967,795

[22] Filed: Dec. 4, 1978

[30] Foreign Application Priority Data

Dec. 7, 1977 [GB] United Kingdom ............... 50937/77

[51] Int. Cl.³ .............................................. A61F 1/00
[52] U.S. Cl. ..................................... 3/1.91; 128/92 C
[58] Field of Search ................... 3/1.9–1.911; 128/92 C

[56] References Cited

U.S. PATENT DOCUMENTS

| | | | |
|---|---|---|---|
| 4,041,550 | 8/1977 | Frazier | 3/1.91 |
| 4,094,017 | 6/1978 | Matthews et al. | 3/1.911 |

FOREIGN PATENT DOCUMENTS 2452412  5/1976  Fed. Rep. of Germany ............ 3/1.911

Primary Examiner—Ronald L. Frinks
Attorney, Agent, or Firm—Cushman, Darby & Cushman

[57] ABSTRACT

An endoprosthetic device for replacing the patellar articular surface is provided in multi-part constructional form and comprises: a first part adapted for securement in the posterior region of the patella, and a second part separately connected with said first part and having an exposed surface shaped to simulate the patellar articular surface. This device can be used for replacement of the patellar articular surface in isolation, and can be subsequently modified, when appropriate, by replacement of the second part for accommodation with a fuller replacement of articular surfaces in the knee joint. Conveniently, the afore-mentioned parts have aligned bores and are interconnected by a replaceable snap-fit third part.

8 Claims, 8 Drawing Figures

ENDOPROSTHETIC PATELLAR DEVICE

This invention concerns endoprosthetic devices for replacing the articular surfaces of bone joints and more particularly such devices for patellar surface replacement.

Devices of the last kind have already been proposed for use in association with other devices for replacement of the femoral and tibial surfaces in the knee joint. This normally involves the provision of three components for respective securement with the relevant bones, with each component being of one-piece construction and with the overall design of the components in terms of material, size and geometry being largely determined by the desired functional inter-relationship between the components. However, there are circumstances in which it might be appropriate to use a patellar component alone in what is termed a partial joint replacement. Moreover, these circumstances will often be such that a subsequent requirement for total knee joint replacement can be expected in the course of time.

It will be appreciated from these comments that the use of a patellar component alone will frequently pre-empt a subsequently required judgement as to the best choice of components for total knee joint replacement, and an object of the present invention is to obviate this predicament.

According to the present invention there is provided an endoprosthetic patellar device of multi-part construction comprising a first part adapted for securement in the posterior region of the patella, and a second part separably connected with said first part and having an exposed surface shaped to simulate the patellar articular surface.

Given the production of a range of the proposed devices and parts therefor with like adaptation for connection but a variety of articular surface simulation, it is possible to use one form of device for the purposes of partial joint replacement, and subsequently to interchange the second part of the device for the purposes of total joint replacement.

In order that the invention may be more fully understood the same will now be further described, by way of example with reference to the accompanying drawings, in which.

Figure 1:
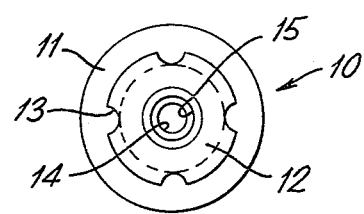
FIGS. 1 and 2 are respective end and side elevations of the first part of one embodiment of the invention.
Figure 2:
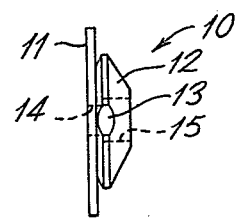
Figure 3:
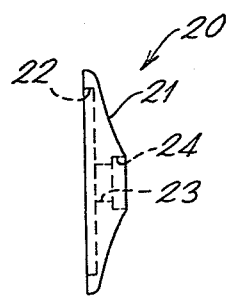
FIGS. 3 and 4 are respective side and end elevations of the second part of such embodiment.
Figure 4:
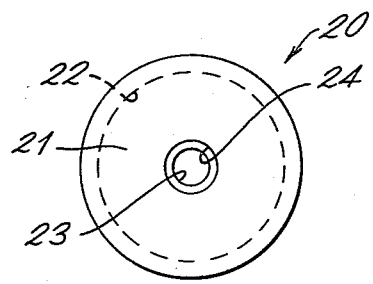
Figure 5:
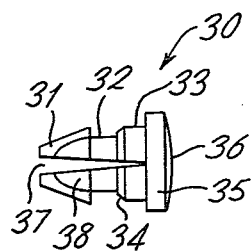
Figure 6:
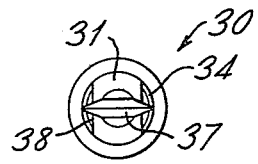
Figure 7:
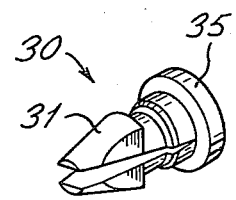
Figure 8:
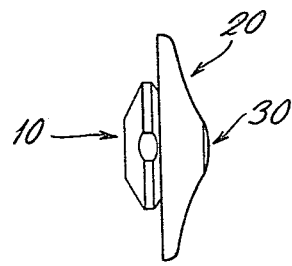

FIGS. 5, 6 and 7 respectively show a third part of the same embodiment in side elevation, end elevation, and perspective view, and FIG. 8 is a side elevation of said embodiment with its three parts mutually connected.

The illustrated first part is denoted generally as 10 and comprises a circular plate 11 from one side of which coaxially projects a body of revolution 12. The body 12, as seen in side view, diverges from the plate up to a maximum diameter which is less than that of the plate, and thereafter tapers away from the plate. The body is formed with a plurality of radial notches 13 uniformly spaced around its maximum circumference. The part 10 is formed with two interconnected bores, one of lesser diameter axially through the plate 11 at 14, and the other of greater diameter axially through the body 12 at 15.

The illustrated second part is denoted generally at 20 and is of generally frusto-conical shape, but with the generator of the part-conical surface 21 being slightly concave over most of its length except adjacent the conical base where the generator is rounded to terminate in generally parallel alignment with the conical axis. The part 20 is formed with a recess 22 in its base which recess is complementary to the plate 11 of part 10 to receive such plate coaxially in the part 20, and axially bored through at 23 to a diameter greater than that of of the bore 14 in part 10, the bore 23 being itself formed with a counterbore 24 from the narrow end of the part 20.

The illustrated third part is a clip denoted generally as 30 and this serves to connect the first and second parts together as described below. The part 30 is largely formed as a body of revolution having, in succession from the left as seen in FIG. 5, a frusto-conical retainer portion 31, a circular cylindrical neck portion 32 joining the wider end of retainer portion 31, a circular cylindrical inner head portion 33 formed with a chamfer 34 around its edge adjacent portion 32, and an outer head portion 35 which is circular cylindrical except that its free end face 36 is convexly part-spherically shaped. The part 30 is formed with a wedge-shaped slot 37 convergently extending from the narrow free-end face of retainer portion 31 to the junction between the head portions 33 and 35, the slot 37 being symmetrically disposed about an axial diametral plane of the part 30. Also, the retainer portion 31 is reduced in width over a length from its wider end to a point part way therealong to provide diamtrically-opposed parallel like planar faces 38, which faces are perpendicular to the diametral plane of the slot 37. The maximum diameters of the successive portions 31, 32, 33 and 35 are substantially equal to those of the bores 15, 14, 23 and 24 respectively, the slot 37 has a thickness adjacent the wider end of portion 31 which is similarly equal to the difference between the first two of such diameters, and the distance between the faces 38 substantially equals the diameter of the neck portion 32.

Each of the illustrated parts will normally be of one-piece construction and the first two parts can each be of any biocompatible material suited to the relevant securement and articulatory functions. Typically such materials can be metal, such as stainless steel or chrome-cobalt—molybdenum alloy, or plastics material, such as ultra high molecular weight polyethylene, but other materials, such as ceramics, are possible. However, the third part is to be resilient to allow transient closure of the slot 37, preferably by manual action by way of finger-applied pressure, and this will normally necessitate manufacture from plastics material.

The manner in which the parts are assembled is largely self-evident from the foregoing description and consideration of FIG. 8. This assembly involves receipt of the plate 11 of part 10 into the recess 22 of part 20, and then application of part 30 into the aligned bores of the former two parts, with the conical portion 31 leading into the bore 24. Appropriate force in such application causes closure of the slot 37 as the conical portion 31 passes through bore 14, until portion 31 is wholly received in bore 15 to spring open. The part 30 is dimensioned and shaped to substantially fill the bores of the other parts and it will be seen from FIG. 8 that the convex face 36 of the part 30 blends smoothly with the surface 21 of the part 20 to provide an overall surface simulating the patellar articular surface.

In practice, assembly of the device will normally be effected after the part 10 has been secured in the patella. This securement involves suitable resection and recessing of the posterior face of the patella to receive the body 12 for location in the recess in association with acrylic cement or other gap-filling medium. The part 10 should, of course, be secured in such a disposition relative to the patella that the device can then be assembled with the surfaces 21 and 36 suitably positioned for the desired articular function.

Lastly, regarding the illustrated embodiment, it is to be noted that the device can be removed by drilling away sufficient of the part 30 to allow its disposal and interchange of part 20 for a corresponding part which is to be assembled with part 10 in the same manner by use of a further part 30. Manufacture of part 30 from plastics material facilitates its removal by drilling.

I claim:

1. An endoprosthetic patellar device of multi-part construction comprising:
    a first part adapted for securement in the posterior region of the patella,
    a second part separably connected with said first part and having an exposed surface shaped to simulate the patellar articular surface, and
    a third part interconnecting said first and second parts, said first and second parts being formed with axially aligned bores, and said third part being engaged by a snap-fit in said bores.

2. A device according to claim 1 wherein said first and second parts respectively have mutually adjacent portions of complementary form located one within the other.

3. An endoprosthetic patellar device of multi-part construction comprising:
    a first part adapted for securement in the posterior region of the patella,
    a second part separably connected with said first part and having an exposed surface of generally frusto-conical shape with the generator of such shape being slightly concave over most of its length, and
    a third part interconnecting said first and second parts, said third part having a convexly rounded end face located to smoothly continue said frusto-conical shape at its apex.

4. A device according to claim 3 wherein said first part is substantially in the form of a body of revolution defining a surface for said securement which first diverges radially and then tapers relative to progression along the axis of revolution of said body.

5. A device according to claim 4 wherein said body is formed with radial notches distributed around the circumference of maximum diameter of said body surface.

6. A device according to claim 1, 2, 3, 4, or 5 wherein said first part is made of metal, and said second and third parts are each made of plastics material.

7. An endoprosthetic patellar device substantially in the form of a body of revolution comprising a first part for securement in the posterior region of the patella and which first diverges radially and then tapers relative to progression along the axis of revolution of said body, and a second part defining a patella-articular-simulating surface of generally frusto-conical shape with the generator of such shape being slightly concave over most of its length, the base of such shape being adjacent said first part, and the apex of such shape being convexly rounded.

8. A device according to claim 7 wherein said first part is formed with radial notches distributed around the circumference of maximum diameter of said body surface.

* * * * *